US00PP36741P2

(12) United States Plant Patent
Gasic

(10) Patent No.: US PP36,741 P2
(45) Date of Patent: Jun. 17, 2025

(54) PEACH TREE NAMED 'CaroRes Delight'

(50) Latin Name: *Prunus persica*
Varietal Denomination: CaroRes Delight

(71) Applicant: CLEMSON UNIVERSITY RESEARCH FOUNDATION, Clemson, SC (US)

(72) Inventor: Ksenija Gasic, Clemson, SC (US)

(73) Assignee: CLEMSON UNIVERSITY, Clemson, SC (US)

( * ) Notice: Subject to any disclaimer, the term of this patent is extended or adjusted under 35 U.S.C. 154(b) by 0 days.

(21) Appl. No.: 18/738,378

(22) Filed: Jun. 10, 2024

(51) Int. Cl.
*A01H 5/08* (2018.01)
*A01H 6/74* (2018.01)

(52) U.S. Cl.
USPC ..... Plt./197

(58) Field of Classification Search
USPC ..... Plt./197
CPC ..... A01H 5/08; A01H 5/00; A01H 6/7463; A01H 6/74
See application file for complete search history.

(56) References Cited

PUBLICATIONS

Okie et al. "BY520-9, A Peach Rootstock for the Southeastern United States that Increases Scion Longevity", HortScience 29 (6), 1994, pp. 705-706.
Peach Breeding at Clemson University: 10 Years of Progress, 2018 Commercial Peach Production Meeting, Jan. 22, 2019, 22 pages.
Peach Breeding at Clemson University: 10 Year of Progress, Southeast Regional Fair Conference, Jan. 22, 2019, 22 pages.
Gasic, Ksenija "Clemson Peach Breeding Program", Michigan Spring Peach Meeting, Mar. 10, 2021, 33 pages.
Gasic, Ksenija "Developing New Peach Cultivars for the Eastern U.S.", 2021 Mid-Atlantic Fruit and Vegetable Convention, Feb. 10, 2021, 37 pages.
Gasic, Ksenija "Glimpse into the future: New selections from Clemson peach breeding program", 2021 South East Regional Virtual Fruit and Vegetable Conference, Jan. 2021, 30 pages.
Gasic, Ksenija "Glimpse into the future: New selections from the Clemson peach breeding program", Jan. 26, 2021, 24 pages.
Gasic, Ksenija "Peach Breeding Update", Peach session 2, Mar. 4, 2021, 36 pages.
"Advanced Selections In Replicated Trials", Clemson University Peach Breeding Program, Feb. 15, 2022, 17 pages.
Coneva et al. "Performance of Bacterial Spot Tolerant Advanced Peach Selections In Alabama", Jul. 2022, 1 page.
Gasic et al. "Promising selections and upcoming release from the Clemson breeding program", 2023 Upstate peach grower meeting, Feb. 9, 2023, 21 pages.
Gasic et al. "Promising selections and upcoming releases from the Clemson breeding program", Jan. 26, 2023, 19 pages.
Gasic et al."Promising selections and upcoming releases from the Clemson breeding program", 2023 SE Regional Fruit and Vegetable Conference, Jan. 2023, 34 pages.
Gasic "Performance of CaroRes Wonder (SC2), CaroRes Delight (SC9) and EveRes Ruby (SC1) compared to standard cultivars" 2023, pp. 2.
Coneva et al. "'CaroRes Wonder'—New Bacterial Spot Tolerant Peach Cultivar", Jul. 31, 2024, pp. 3.
Gasic "CaroRes and EveRes peach cultivar series from Clemson University" 2024 SE Regional Fruit and Vegetable Conference, Jan. 9, 2024, pp. 4.

*Primary Examiner* — June Hwu
(74) *Attorney, Agent, or Firm* — Fredrikson & Byron, P.A.

(57) ABSTRACT

A new and distinct peach tree (*Prunus persica*) denominated 'CaroRes Delight' can be distinguished by its firm melting yellow flesh, early ripening season, large size, attractive appearance, high red skin color, excellent fruit quality, good flavor, and fruit resistance to bacterial spot disease.

3 Drawing Sheets

Latin name of the genus and species of the plant: *Prunus persica.*
Variety denomination: 'CaroRes Delight'.

BACKGROUND

A new and distinct peach cultivar named 'CaroRes Delight' is described herein. The new cultivar originated from a cross between white flesh peach 'Scarletpearl' (not patented) and yellow flesh pollen parent 'Rubyprince' (not patented) in 2010 near Seneca, SC. This new cultivar was selected in 2013 for its potential as a fresh-market peach in South Carolina and the southern United States. 'CaroRes Delight' can be distinguished by its distinctly juicy melting flesh, early season ripening, large size, attractive appearance, 90% red skin color, excellent classic peach flavor, and high tolerance to bacterial spot and brown rot disease.

Seneca, SC is under a humid subtropical climate. Winters are short and mild with little to no snow; summers are long, hot and humid. There is significant annual rainfall averaging 1339 mm (52.7 in) coming from an average of 116 rainy days a year. July has the greatest number of rainy days (13.8 d), mostly from thunderstorms, with an average of 88.9 mm (3.5 in) and rarely exceeding 175 mm (6.9 in) or falling below 33 mm (1.3 in). Average high temperature in the warmest month, also July, is 32° C., with an average heat index at 40° C. The average low temperature in the coldest month, January is 0.8° C. The hours below 7° C. varies greatly year to year, but range between 700-1200 hours.

The original plant selection was propagated asexually by budding onto standard peach rootstock cultivar Guardian® (not patented) and a test plot of two plants was established in Seneca, SC. Subsequently, larger test plantings were established with asexually multiplied plants at two additional locations in South Carolina (near Ridge Springs, SC). At each location, propagation was by budding onto the standard peach rootstock cultivar Guardian® (not patented) from buds collected at the test plot in Seneca, SC. No incompatibility or change of scion attributes with Guardian® (not patented) peach rootstocks have occurred following budding. During all asexual multiplication, the characteristics of the original plant have been maintained and no aberrant phenotypes have appeared. The asexual multiplication demonstrates that such reproduction of the characteristics of the tree are consistent and are established or transmitted through succeeding generations.

BRIEF SUMMARY

The new and distinct peach cultivar originated from a cross between 'Scarletpearl' (not patented) and 'Rubyprince' (not patented) made in 2010 near Seneca, SC. The seeds resulting from this controlled hybridization were germinated in a greenhouse in the late winter 2010/early spring of 2011 and planted in a test field in Seneca, SC. The seedlings fruited during the summer of 2013 and one peach seedling, designated SC10-13-178 was selected for its juicy melting flesh, early season ripening, large size, attractive appearance, excellent classic peach flavor, and tolerance to bacterial spot disease. The new cultivar, designated originally as SC10-13-178, tested as SC9, was subsequently named 'CaroRes Delight'.

The claimed variety differs from its parents, 'Scarletpearl' (not patented) and Rubyprince (not patented) in that while 'CaroRes Delight' fruit has yellow flesh, which is similar to 'Rubyprince' (not patented), the "CaroRes Delight' fruit is different than 'Scarletpearl' (not patented) which has white flesh. The 'CaroRes Delight' has superior size, averaging 71 mm compared to Rubyprince (not patented) at 67 mm, and is less prone to pit splitting than both parents. The present variety of peach tree when compared to the seed parents is similar in appearance to 'Rubyprince' (not patented) in that the 'CaroRes Delight is a yellow fleshed peach with a firm but melting texture, but superior due to excellent eating quality and a high level of tolerance to both foliar and fruit infection of bacterial spot (*Xanthomonas campestris* pv. *Pruni* (Smith) Dye).

BRIEF DESCRIPTION OF THE PHOTOGRAPHS

The accompanying photographs show typical specimens of the new cultivar in color as nearly true as it is reasonably possible to make in a color illustration of this character.

DETAILED DESCRIPTION OF THE NEW CULTIVAR

Figure 1:
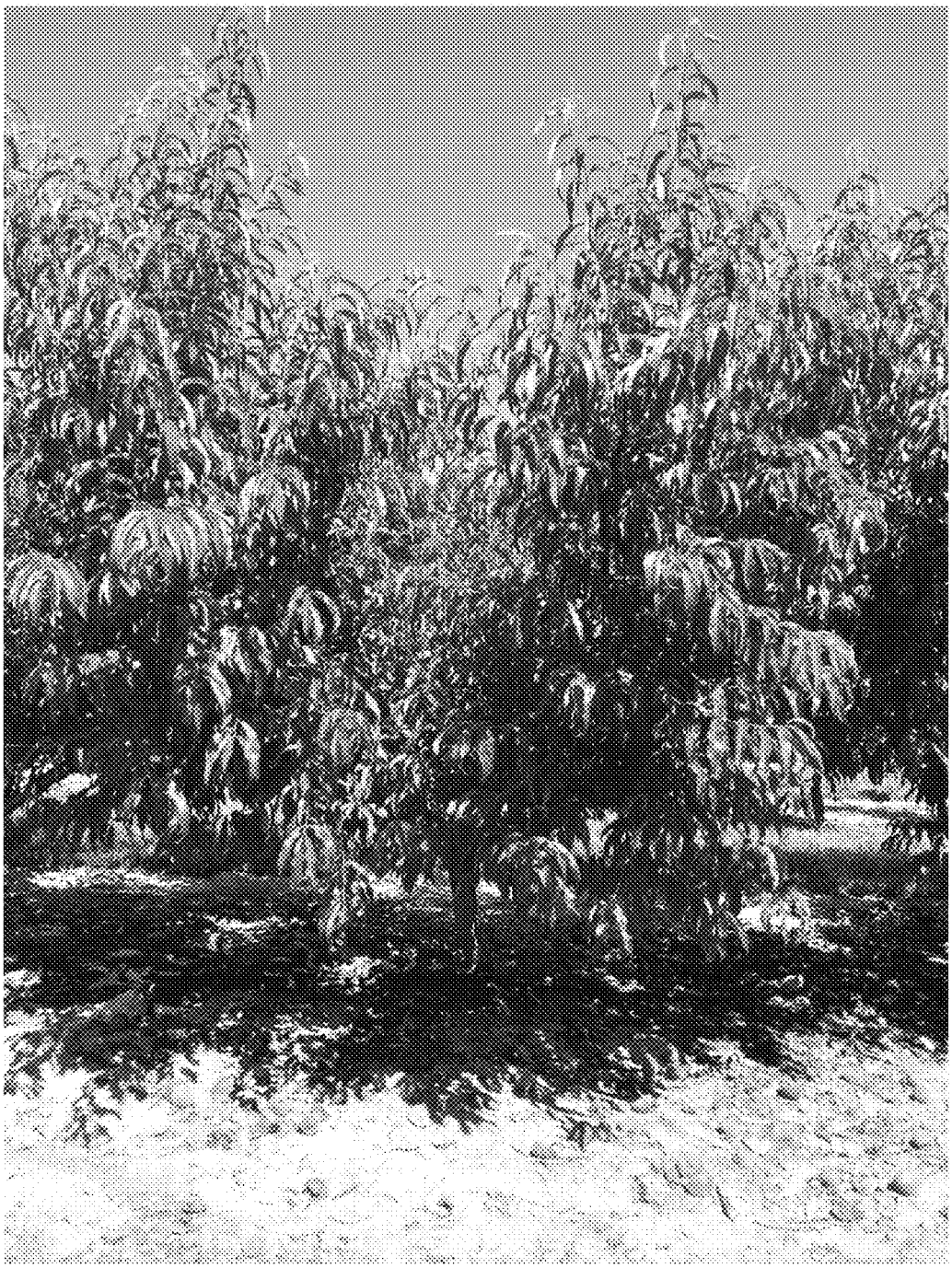
FIG. 1 is a photograph of a tree with mature fruit of 'CaroRes Delight' at ten years of age.
Figure 2:
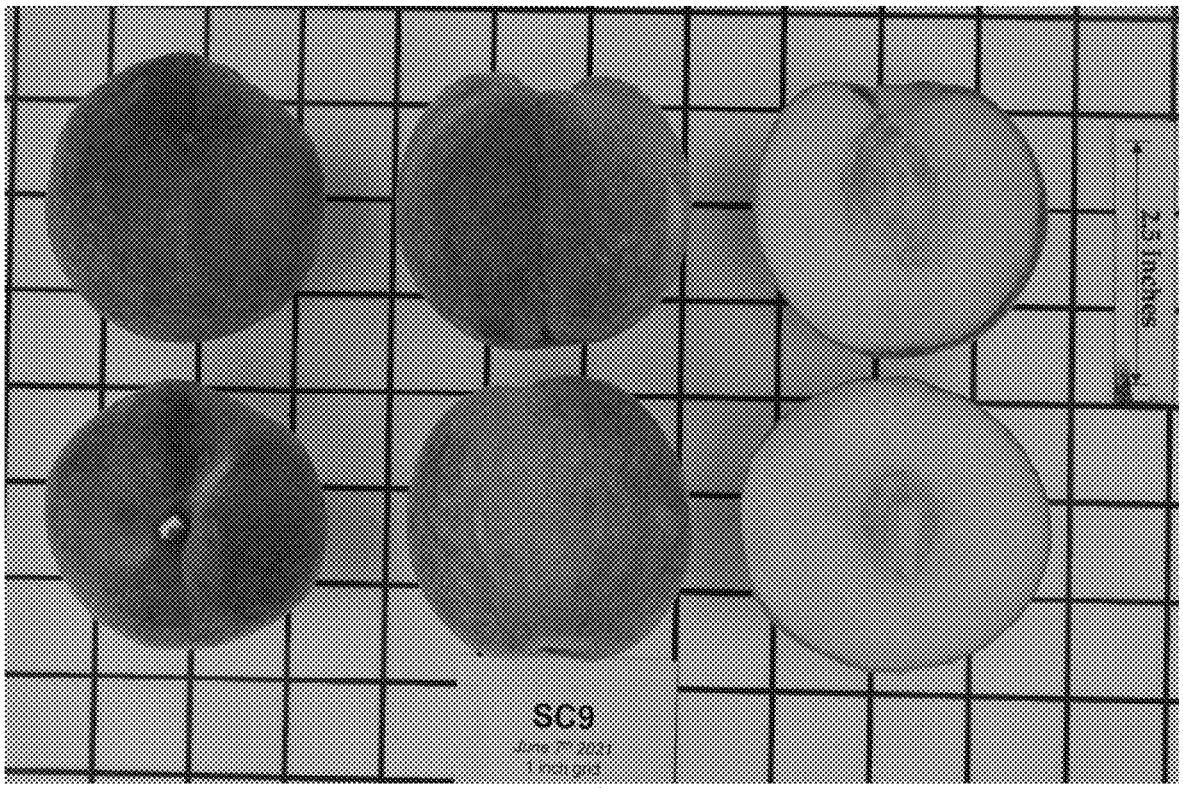
FIG. 2 is a photograph of a whole and longitudinally cut fruit of 'CaroRes Delight' at maturity at ten years of age.
Figure 3:
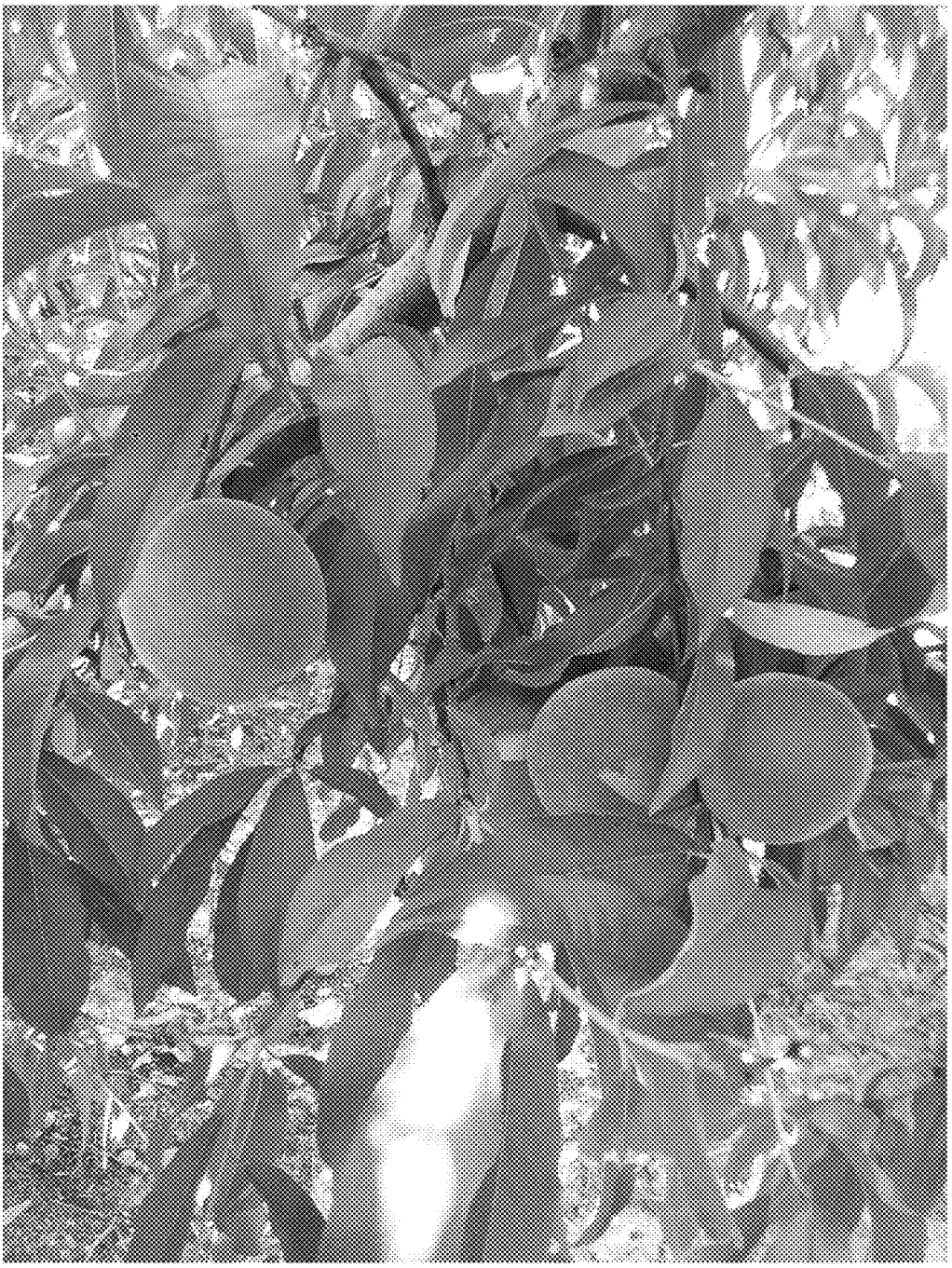
FIG. 3 is a photograph of fruit on the tree of 'CaroRes Delight' at ten years of age.

Plants and fruit of this new cultivar differ phenotypically from its parents and cultivars ripening at the similar time. While 'CaroRes Delight' has yellow melting flesh textured like its pollen parent, Rubyprince (not patented), it ripens about a week earlier, and has superior size, averaging 71 mm compared to Rubyprince (not patented) at 67 mm, and 'Carored' (not patented) 66 mm, and is less prone to pit splitting. 'CaroRes Delight' is different than its maternal parent 'Scarletpearl' (not patented) which has white flesh, and 'CaroRes Delight' having yellow flesh. 'CaroRes Delight' has moderate chill requirement (850 hours), which is similar to pollen parent 'Rubyprince' (not patented) and higher than 'Carored' (not patented) (650 hours), but 'CaroRes Delight' blooms 1-2 weeks later and has high fruit and leaf tolerance to bacterial spot (*Xanthomonas arboricola* pv. *pruni*).

Trees of the new cultivar are vigorous, productive, standard in size, well-branched and symmetrical with an upright to semi-spreading growth habit, comparable to other peach and nectarine trees. Trees express a high level of tolerance to both foliar and fruit infection of bacterial spot [*Xanthomonas campestris* pv. *pruni* (Smith) Dye]. The new cultivar blooms in the spring around the beginning to middle of March, one week later than 'Carored', which is on the middle to late range of all cultivars blooming in Seneca, SC. No winter cold injury has been observed on wood or buds of the new cultivar in South Carolina tests where minimum temperatures have reached 5° F. (−15° C.) during evaluation. Bud chill hardiness ranges from −10 to −12° C. Chilling requirement to break dormancy is estimated to be between 700-800 hours below 45° F. (7° C.), which is similar to pollen parent 'Rubyprince' (not patented), 850 chill hours, but higher than 'Carored', 650 chill hours.

Fruit of the new cultivar ripens early season, averaging 3-10 days before 'Rubyprince' (not patented) and 7-10 days after 'Carored' (not patented). Average first ripening date is June $6^{th}$ in upstate South Carolina (near Clemson). Very few split pits, less than 'Rubyprince' (not patented) and 'Carored' (not patented), with uniform shape, but with some fruit with lopsided halves and no tips. Fruit yields have been good with an estimated 57.82 kg total yield on $4^{th}$ leaf, open center trees.

The fruit is very round in shape. Fruits are attractive with around 90% Dark Red (RHS 183A) blush. The fruit skin has light pubescence, less than pollen parent 'Rubyprince' (not patented) and 'Carored' (not patented). The flesh of the fruit is brilliant yellow (RHS 11A) in base color with vivid reddish orange (RHS N30A) in flesh close to skin. Flesh is of the melting type, but fruit holds well on tree which is similar to the pollen parent 'Rubyprince' (not patented) but different than fruit of the cultivars within similar ripening time such as 'Carored'. The fruit is a clingstone, in that the flesh adheres to the pit. Fruit size is large averaging 204 g. 'CaroRes Delight' has the higher pack out of fruits larger than 2¾ in (>90%) compared to pollen parent 'Rubyprince' (not patented) 40%, and other cultivars ripening at the similar time, 'Carored' (not patented) 30% and 'Summerprince' (not patented) 15%. 'CaroRes Delight' had no fruit smaller than 2 and ½ in, which is standard size for early ripening cultivars such as 'Carored' (not patented), 70% of fruit smaller than 2½ in and 'Summerprince' (not patented) 55% fruit smaller than 2½ in. The fresh fruit has excellent classic peach flavor and was rated highly in evaluations. Fruits average 10.1% soluble solids, which is good for the season. Flavor is sweet and well balanced with moderate acidity. The acidity level of 'CaroRes Delight' is 0.91% malic acid.

The following is a detailed description of the botanical and pomological characteristics of the subject peach. Color data are presented in Royal Horticultural Society Colour Chart designations (2015 $6^{th}$ revised edition). Where dimensions, sizes, colors, and other characteristics are given, it is to be understood that such characteristics are approximations of averages set forth as accurately as practical.

Plants used for botanical data were at their $4^{th}$ leaf and grown on berms on a fine sandy loam soil with stake irrigation near Clemson, SC. Trees were trained to an open-center training system and dormant pruned annually. Fruits on all trees were thinned to approximately 6 inches between fruits 4-5 weeks after full bloom. The trees were fertilized near budbreak (late March on average) with 19-19-19 fertilizer. Weeds were controlled with pre- and postemergence herbicides. Routine commercial fungicide and insecticide applications were made to the trees. The descriptions reported herein are from specimens grown near Clemson, SC.

Plant:

*Size*.—Mature trees ($4^{th}$ leaf) average 2.88 m in height and 4.26 m in spread or width, and a semi-upright growth habit, as grown on Guardian® (not patented) rootstock using an open-center training system commonly used on peaches.

*Growth*.—Vigorous, symmetrical form, good canopy development.

*Productivity*.—Good productivity and consistent from year to year. High bud density, and fruit set. Yields averaged 57.82 kg/tree for 'CaroRes Delight' similar to 'Carored' (not patented) at 62.34 kg/tree.

*Cold hardiness*.—Wood and dormant buds hardy to 5° F. (−15° C.). This was the coldest temperature that the trees were exposed to at the test site, but hardiness may exceed this temperature.

*Disease resistance*.—Leaves and fruit tolerant but not immune to bacterial spot under growing conditions where bacterial spot infection is often very severe on susceptible genotypes. A commercial fungicide program was utilized in orchards used in the development and evaluation of the instant cultivar, thus no resistance to brown rot (*Monilinia fructicola* (G. Winter) Honey) or scab (*Fusicladium carpophilum* (Thum.) Oudem), the other common diseases at Clemson, SC, were determined.

*Insect resistance*.—Insecticides were applied to orchards used in the development of the instant cultivar to control the common insects at the location including oriental fruit moth (*Grapholita molesta* (Busck)), plum curculio (*Conotrachelus nenuphar* (Herbst)), stinkbug (*Halyomorpha halys* (Stal); *Euschistus servus* (Say); *Acrosternum hilare* (Say); *Nezara viridula* (Linnaeus); *Thyanta* spp.), tarnished plant bug (*Lygus lineolaris* (Palisot de Beauvois)), lesser peach tree borer (Synathedon pictipes (Grote & Robinson)), and greater peach tree borer (*Synanthedon exitiosa* (Say)). Therefore, no insect resistance was determined in the testing of the instant cultivar.

Foliage/shoots/branches:

*Shoots*.—Smooth. Dormant-season shoot (branch): length 43.48 cm; diameter at base 0.54 cm; diameter at midpoint 0.34 cm; diameter at terminal 0.26 cm. Dormant-season shoot color top: Dark Red (N187A); bottom: Green Group (143C).

*Branches*.—Length 63.5 cm; diameter at base 0.42 cm; diameter at midpoint 0.3 cm; diameter at terminal 0.2 cm.

Leaves: Simple, alternate, glabrous, lanceolate, petiolate, and deciduous. Venation pinnate; base acute; terminal or apex acuminate; margin serrated. Mature leaf size: length 15.5 cm; width midpoint 3.8 cm. Leaf serrations 6.2/cm. Mature leaf color: abaxial—Moderate Olive Green (147A); adaxial—Grayish Olive Green (NN137B); abaxial—red mid-vein absent. Young leaf color: abaxial—Strong Yellow Green (144A); adaxial—Moderate Olive Green (146A); Petiole length—mature leaf: 1.2 cm, petiole width: 2 mm; petiole texture: smooth no pubescence; petiole strength: strong. Leaf glands: globose, average of 1.6 per leaf, located at base of leaf blade at top of petiole. Leaf glands are 0.09 cm in length and 0.09 mm in diameter. Stipule length: 14 mm, width: 0.5 mm. Beginning of leaf bud burst—Julian 69 (March 10).

Buds: Number of leaf buds per 15 cm: 10.4, evenly distributed along the shoot. Number of flower buds per 15 cm from terminal: 18.2. Mature shoot internode length: base 2.1 cm, midpoint 2.9 cm, terminal 1.9 cm.

Bark (of mature trunk of tree):

*Color*.—Dark Greyish Yellowish Brown (N199B).

*Texture*.—Rough.

Trunk:

*Diameter*.—16.26 cm (at 25 cm above ground level).

Flower buds: Dormant flower bud length 0.5 cm and diameter 0.25 cm and color Red Purple Group (59A); dormant buds swell and expand in late winter and increase in size during this expansion to fully open flowers.

Flowers: Bloom occurs prior to vegetative bud break; solitary to occasional double individual flowers at a single node; perfect; self-fertile.

*Date of bloom*.—50%, Julian 64 (March 5); 90%, Julian 70 (March 11) which is early to mid-bloom period for all cultivars in Seneca, SC; Rubyprince (not patented) 90%, Julian 74 (March 15).

*Size*.—Diameter fully open 4.2 cm.

*Type*.—Showy.

*Color*.—Adaxial/abaxial: Strong Purplish Pink (55-B)/Strong Purplish Pink (55B).

*Petals per flower*.—5 (10 when doubled); length 21.6 mm; width 17.2 mm; texture smooth; shape teardrop.

*Length of pistil*.—1.9 cm; positioned below anthers and above petals and stamen.

*Width of pistil*.—1 mm.

*Stamens*.—Average 48.2/flower with pollen present, fertile and abundant.

*Ovary*.—Pubescence, globose to oval. Brilliant Yellowish Green (140C).

Fruit:

*Size*.—Large, avg. 204 g. Diameter stem end 6.8 cm, equator 7.4 cm, blossom end 6.8 cm; length base to apex 6.8 cm.

*Shape*.—Round.

*Mucron tip at pistil end*.—Mucron tip at pistil end — absent, shape — weakly pointed; fruit symmetry from pistil end — symmetric.

*Skin*.—Light pubescence, attractive; thickness — thin; ground color Moderate Reddish Orange (35A) with red blush (Dark Red 183A) covering over 90% of surface on average; overcolor pattern — solid blush.

*Flesh*.—Color Brilliant Yellow (11A) with Vivid Reddish Orange (N30A) close to skin; clingstone; uniform ripening, melting texture. Firmness 2.99 $kg/cm^2$. Classic peach flavor, sweet, and moderate acid. Anthocyanin intensity: next to the fruit skin — medium; central part weak; around stone — weak. Fruit flesh fiber — absent.

*Pedicel length.*—0.78 cm.

*Pedicel diameter.*—0.52 cm.

*Pedicel color*.—Moderate Reddish Brown (74A).

*Pedicel strength*.—Strong; holds on well.

*Ripe date*.—June 7$^{th}$ (Julian 158) in upstate South Carolina; 'Rubyprince' (not patented) ripens June 13$^{th}$ (Julian 164). Ripening of individual fruit is uniform.

*Tendency of pit to split*.—Light splitting. Less splitting than 'Rubyprince' (not patented).

*Soluble solids.*—9.9%.

*Fruit juice pH.*—3.5.

*Fruit juice titratable acidity*.—0.91% malic acid.

*Fruit glossiness*.—Weak.

*Storage performance*.—Overall for 0-2 weeks of storage 'CaroRes Delight' performs well and shows no loss in fruit quality.

Pit/stone:

*Size*.—Length 3.7 cm; diameter (midpoint) 2.9 cm.

*Shape*.—Oblong, truncate base, unequal side, furrowing and pitting.

*Color*.—Pale Orange Yellow (159B) when flesh freshly cut.

Kernel:

*Size*.—Length 2.1 cm; diameter 1.4 cm.

*Shape*.—Ovate with acute tip and obtuse base.

*Color*.—Pale Greenish Yellow (13D) when fresh.

Uses: Fresh consumption, not evaluated for drying or other uses.

The cultivar: The outstanding characteristics of 'CaroRes Delight' are attractive appearance, yellow fleshed peach, firm but melting texture, and bacterial spot tolerance. 'CaroRes Delight' stands out from other cultivars that are ripening at the similar time due to excellent eating quality, firmness, consistent large size, high pack-out and tolerance to disease.

I claim:

1. A new and distinct cultivar of peach tree named 'CaroRes Delight,' substantially as herein illustrated and described.

* * * * *